(12) United States Patent
Antonelli et al.

(10) Patent No.: US 8,177,721 B2
(45) Date of Patent: *May 15, 2012

(54) REMOTE BLOOD PRESSURE WAVEFORM SENSING METHOD AND APPARATUS

(75) Inventors: Lynn T. Antonelli, Cranston, RI (US); Candida L. Desjardins, Dartmouth, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 1017 days.

This patent is subject to a terminal disclaimer.

(21) Appl. No.: 12/131,472

(22) Filed: Jun. 2, 2008

(65) Prior Publication Data

US 2009/0299197 A1 Dec. 3, 2009

(51) Int. Cl.
*A61B 5/02* (2006.01)

(52) U.S. Cl. ........ 600/485; 600/481; 600/504; 600/513; 600/527; 367/87; 367/199

(58) Field of Classification Search .................. 600/481, 600/485, 504, 513, 527; 367/87, 198, 199
See application file for complete search history.

(56) References Cited

U.S. PATENT DOCUMENTS

| | | | |
|---|---|---|---|
| 7,128,714 B1 * | 10/2006 | Antonelli et al. | 600/485 |
| 7,539,083 B2 * | 5/2009 | Blackmon et al. | 367/198 |
| 2005/0049582 A1 * | 3/2005 | DeBenedictis et al. | 606/9 |

* cited by examiner

*Primary Examiner* — Gail R Gabel
(74) *Attorney, Agent, or Firm* — James M. Kasischke; Jean-Paul A. Nasser; Michael P. Stanley

(57) ABSTRACT

The invention as disclosed is a non-contact method and apparatus for continuously monitoring a physiological event in a human or animal, such as blood pressure, which involves utilizing a laser-based interferometer system in combination with a laser tracking system and a signal processor to produce a waveform that is representative of a continuous physiological event such as blood pressure or respiration in a subject.

11 Claims, 5 Drawing Sheets ical events.

REMOTE BLOOD PRESSURE WAVEFORM SENSING METHOD AND APPARATUS

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER PATENT APPLICATIONS

None.

BACKGROUND OF THE INVENTION (1) Field of the Invention

The present invention relates generally to a method and apparatus for measuring and monitoring physiological events in humans and animals, and more particularly to a non-contact, non-invasive method and apparatus for continuously measuring and monitoring physiological events in humans or animals using a laser Doppler vibrometer to create waveforms which are directly related to the physiological events.

(2) Description of the Prior Art

The measurement of physiological events, such as blood pressure, heart rate, temperature and respiratory rate, is fundamental to determining the fitness and wellbeing of humans and animals. The continuous recording and analysis of an accurate blood pressure waveform identifies important events in the cardiac cycle, such as a subject's heart rate, the timing of peak systole, the dicrotic notch, the pre-ejection period (PEP) and the left ventricular ejection time (LVET). The location of the dicrotic notch indicates the closure of the aortic valve, which occurs at the end of left ventricular ejection, representing the end of the systolic phase and the start of diastole and left ventricular relaxation. Information about the systolic time intervals is useful in assessing cardiac condition and various disease states, including left ventricular failure, myocardial infarction, coronary artery disease, and valve disorders.

The time intervals of the various stages of the cardiac cycle are also measured to detect changes under cardiac disease conditions and pharmacological influence. For example, continuous monitoring of pre-ejection period and left ventricular ejection time ratios may be utilized to test the effects of drugs, exercise, or other stimuli, whereby an increase or decrease in the ratio may indicate an improvement or worsening of systolic efficiency.

The three basic systolic time intervals are the pre-ejection period (PEP), left ventricular ejection time (LVET) and total electromechanical systole (QS2). Linear relationships between heart rate (HR) and the duration of the systolic phases of the left ventricle (LV) have been derived by observation. These following equations have been utilized in the prior art to predict the durations of the systolic time intervals for normal patient observations based on the heart rate alone:

$$PEP = -0.0004*HR + 0.126 \quad (1)$$

$$LVET = -0.0016*HR + 0.394 \quad (2)$$

$$QS2 = -0.020*HR + 0.522 \quad (3)$$

The dicrotic notch as observed on a blood pressure waveform indicates the occurrence of the closure of the aortic valve and marks the end of left ventricular ejection. This event represents the end of the systolic phase and the start of diastole and left ventricular relaxation. The location of the dicrotic notch on a blood pressure waveform can be used for evaluating the above listed linear regression equations that may be utilized to predict the systolic time interval as a function of heart rate. The regression equations are expected to deviate for patients with cardiac dysfunction.

Traditionally, the measurement of arterial or blood pressure waveforms in humans or animals is done either by noninvasive methods that make physical contact with the patient or by invasive methods that require penetration of a patient's dermis. For example, a noninvasive method of measuring blood pressure in small animals uses a sphygmomanometer cuff wrapped around the subject's foreleg, foot or the base of the tail. As the cuff is being inflated, an ultrasonic probe is used to hear the sounds that correspond to the systolic endpoints that are used to determine the corresponding blood pressure value. This method provides only systolic pressure values for a moment in time, and does not provide a time-continuous pressure waveform. There is not yet a method to measure diastolic pressure in small animals.

Alternatively, an invasive method of measuring blood pressure utilizes a monitoring system having intra-arterial catheters containing miniature pressure transducers for continuous monitoring of arterial pressure waveforms. These devices are also capable of measuring actual pressure amplitudes in time, but by their design are inserted into the arterial system, which may cause distress.

Typically, monitoring of the blood pressure waveform for animals is not routinely done, even though high blood pressure in animals can be symptomatic of a variety of diseases including chronic renal failure, hyperthyroidism, Cushing's disease, diabetes mellitus, acromegaly, Glomerular disease, polycythemia, and pheochromocytoma.

There exists a need to continuously and accurately measure blood pressure without making physical contact with the subject, especially for patients, such as burn victims, neonates, and patients who need to be monitored without disturbing sleep or rest. There is also a need to take such measurements on a subject that may be prone to sporadic movement. The proposed laser-based, non-contact and noninvasive technique is capable of measuring the arterial pressure waveform from which the timing of various events in the cardiac cycle can be determined, without causing additional distress or discomfort.

SUMMARY OF THE INVENTION

It is a general purpose and object of the present invention to provide an improved non-contact blood pressure waveform monitoring apparatus and method.

Another object is to provide a laser-based system that may be utilized to continuously provide highly detailed information about the timing characteristics of the blood pressure waveform.

Another object is to provide a system that does not require elaborate adjustments of one or more lasers and laser detectors so that the system may be quickly utilized.

Another object is to provide a system that is capable of taking measurements from a subject when the subject is moving.

These and other objects, features, and advantages of the present invention will become apparent from the drawings, the descriptions given herein, and the appended claims. However, it will be understood that the above listed objects and/or advantages of the invention are intended only as an aid in understanding aspects of the invention, are not intended to limit the invention in any way, and do not form a comprehensive list of objects, features, and advantages.

The above objects are accomplished with the present invention by a combined implementation of a laser Doppler vibrometer (LDV) as the remote sensor, a signal processing unit, a graphical user interface, a glint tracker and a retro-reflector target to enhance sensor performance. The LDV directs a single output laser beam onto a measurement surface to detect the surface vibration velocity at the point where the laser hits the surface. The measurement surface towards which the laser beam is directed is a section of the subject's skin surface orienting the laser beam such that it is substantially perpendicular to the skin surface at a location wherein the skin surface is moveable in response to a blood pressure pulse, and/or detecting one or more variables related to movement of the skin surface. A low-power (1 mW), continuous, red laser beam is directed onto the measurement surface. By interfering the detected beam that was reflected by the measurement surface with a reference beam within the LDV, a measure of the surface velocity is obtained.

The non-contact method and apparatus may further comprise use of detectors capable of detecting the one or more variables related to movement of the skin surface in a direction substantially parallel to the laser beam and/or producing the blood pressure waveform representation by plotting skin surface velocity with respect to time through the use of a signal processor. The signal processing unit provides skin displacement information, which more directly corresponds to the blood pressure waveform than a measured velocity signal. The blood pressure waveform can be obtained by integrating the velocity signal to obtain surface displacement.

The retro-reflector target provides a practical sensor mount scheme for veterinary use and is used in conjunction with the glint tracker to keep the laser Doppler vibrometer on target when a subject is prone to sporadic movement.

BRIEF DESCRIPTION OF THE DRAWINGS

A more complete understanding of the invention and many of the attendant advantages thereto will be more readily appreciated by referring to the following detailed description when considered in conjunction with the accompanying drawings, wherein like reference numerals refer to like parts and wherein.

DETAILED DESCRIPTION OF THE INVENTION

The present invention provides a non-contact method and apparatus for continuously monitoring physiological events such as the anatomical blood pressure waveform with sufficient accuracy and precision to determine important timing related parameters such as, for example, the left ventricular ejection time (LVET) and pre-ejection period (PEP). For cardiac cyclic timing diagnostic purposes, the timing of the blood pressure waveforms should be measured with sufficient accuracy so that the components of the waveform, e.g., the dicrotic notch, are available for accurate analysis. However, it has been observed by the inventors that cardiac cyclic analysis of the blood pressure waveform does not require absolute values of blood pressure. Thus, while the present technique does not necessarily directly measure or provide absolute values of blood pressure, cyclic analysis of the blood pressure waveform can be readily performed utilizing the data produced by the present invention. Calibration techniques may be utilized as discussed hereinafter to provide absolute values in certain circumstances, if desired.

Figure 1:
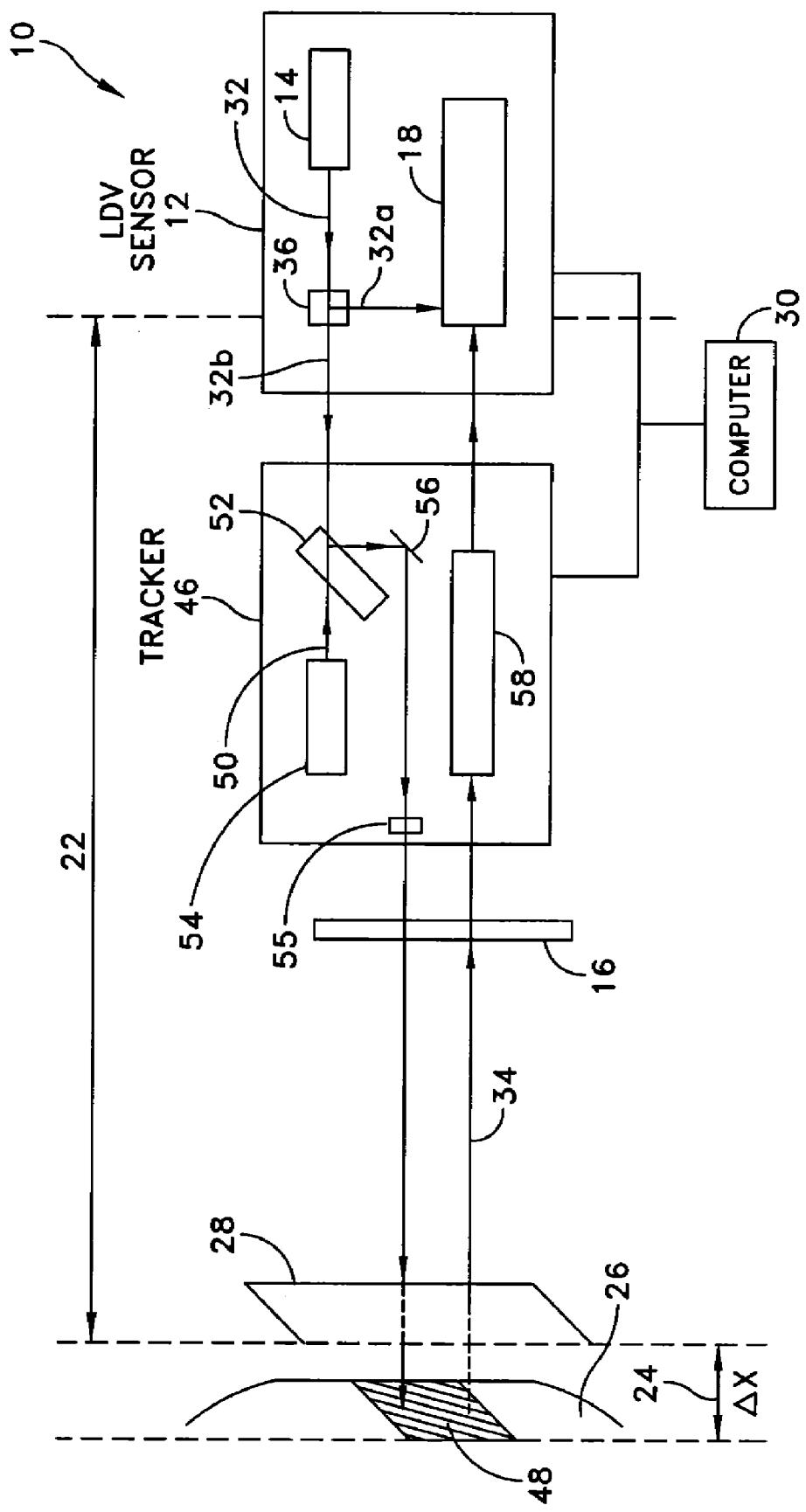
FIG. 1 is a schematic overview of the operation and setup of a non-contact blood pressure waveform monitoring system in accord with one embodiment of the present invention.

Referring now to the drawings and, more particularly, to FIG. 1, there is shown a non-contact blood pressure waveform monitoring system 10 for remotely and continuously measuring the blood pressure waveform of a human or animal through noninvasive means that require no physical contact. Measurements can be done on the skin over any artery that produces a measurable vibration of the skin surface. System 10 utilizes laser Doppler vibrometer sensor 12 to detect the movement of skin on a subject, in this case the skin surface 26 is above a major artery.

Laser Doppler vibrometer 12 comprises laser source 14 capable of emitting a laser beam 32 that travels the distance 22 from laser source 14 to skin surface 26. The laser beam is preferably directed perpendicularly or substantially perpendicularly to skin surface 26. Blood flowing through the artery directly below the skin causes skin surface 26 to pulsate in a rhythm corresponding to ventricular contractions of the subject's heart. Skin surface 26 moves an amount $\Delta x$, as indicated by numeral 24, from its initial position to a position represented by plane 28. The maximum displacement of the skin surface 26 is caused by the peak in the systolic cardiac cycle when the heart (left ventricle) forces the blood volume into the aorta. This corresponds to a peak in the displacement waveform. As the skin surface 26 changes direction and begins to contract, the skin velocity goes to zero during this change in skin direction. $\Delta x$ represents the distance of movement of the plane of skin surface 26 in a direction substantially parallel to the laser beam produced by laser source 14.

The accuracy and reliability of the laser Doppler vibrometer sensor 12 is dependent upon it receiving laser reflections from the measurement surface. A surface with a poor reflective quality will degrade sensor performance by decreasing the detectable signal level and increase the noise. Reduced optical return and poor laser reflection from the skin surface 26 will diminish the velocity amplitude measured by the laser beam 32. One solution is to prepare the skin surface 26 by removing the hair around the detection area. Another alternative is to place a strip of retro-reflective tape 48 on the skin surface 26. The retro-reflective tape 48 can be located above an artery on the subject's neck (carotid artery). The retro-reflective tape 48 can also be located on the subject's leg or on top of the foot, which do not have breathing modes associated with it.

Laser beam 32 is directed at and reflected by retro-reflective tape 48. The reflected laser beam 34 is focused by lens 16 and recovered by detector 18. The reflected laser light beam 34 is modulated by the movement of skin surface 26 by means of a Doppler shift in the optical wavelength, as compared to the original laser beam 32 produced by laser source 14. Detector 18 generates a signal corresponding to the velocity of the pulsatile skin motion as derived from the Doppler shift.

Since the measurement subject may move during monitoring, a means for remote steering of the laser beam 32 onto the desired measurement point on the skin surface 26 can be achieved using a tracker system. A glint tracking system 46 is utilized in conjunction with the placement of the retro-reflective tape 48, to steer the laser Doppler vibrometer sensor's 12 laser beam 32 automatically onto the retro-reflective tape 48. The laser beam 32 is continuously steered onto a position where it will receive a direct reflection from the desired position on the skin surface 26. The glint tracking system 46 uses its own laser beam 50 originating from the tracker light source 54 and directed onto the retro-reflective tape 48, combined with the laser Doppler vibrometer sensor 12 laser beam 32. The laser beam 32 from the laser Doppler vibrometer sensor 12 is directed into the glint-tracking system 46, which is designed to align the laser beam 32 onto the tracker beam 50 through a beam combiner 52 such that both the laser beam 32 and tracker beam 50 are superimposed and both beams take advantage of the motion controlled mirror 56 that provides "mirror steering" of the beams. Both the laser beam 32 and tracker beam 50 are directed onto the surface of the retro-reflective tape 48 placed on the desired skin surface 26 location. The combined laser beam 32 and tracker beam 50 are steered through a search pattern until a reflection from the retro-reflective tape 48 is detected by the tracking beam detector 58. The glint tracking system 46 is used in combination with a programmable computer 30 that serves as the tracking system controller with an active feedback loop dependent upon the tracking beam detector 58 response to continually steer the tracker beam 50 to maintain a lock on the retro-reflective tape 48.

The frequency bandwidth of the laser Doppler vibrometer sensor 12 will be required to be approximately 500 Hz to accommodate various heart rates for both animal and human subjects. For example, certain animals have a heart rate in the range of 60 to 220 beats per minute (bpm) range, depending on the animal type and size.

LDV sensor 12 preferably comprises an interferometer for comparison of the initially produced laser beam (or a reference beam derived there from) with the reflected laser beam. In a preferred embodiment, laser Doppler vibrometer 12 operates by splitting the laser beam 32 with a beam splitter 36 into a reference beam 32a and a sensing beam 32b. The reference beam 32a is frequency shifted by a modulator (not shown) in detector 18 so that the components of detector 18 can discriminate between the direction of motion of the skin surface 26 towards and away from the detector 18. Detector 18 measures the Doppler frequency of the reflected beam 34 as modulated by the movement of skin surface 26. The maximum and therefore optimum reflected signal occurs when laser Doppler vibrometer 12 is oriented such that the laser beam 32 produced by laser source 14 is substantially perpendicular to skin surface 26.

Detector 18 generates a continuous stream of analog output voltages corresponding to the pulsation velocity of skin surface 26. Detector 18 is connected to computer 30 that serves as a signal processor that can digitize, record, and analyze the analog voltage signals as desired. Alternatively, the analog voltage may be fed to a device, such as an oscilloscope for immediate display of the blood pressure waveform. Computer 30 will have a data sample rate equal to or greater than 1 kHz, which is at least twice the maximum detectable frequency of the laser Doppler vibrometer sensor 12 to meet the Nyquist criterion. A sample rate of at least 10 times the Nyquist rate provides a better estimate of the blood pressure waveform.

Computer 30 performs several processing functions to the signal generated by the detector 18. The computer 30 will initially "clean up" the signal to deal with the surface velocity artifacts resulting from combining the laser beam 32 with the tracker system 46 and motion of the subject. The computer 30 will determine the subject's pulse rate from the signal as well as information on the systolic time interval parameters. The computer 30 provides both the velocity signal (sometimes referred to as the impedance waveform) and the displacement signal. The computer 30 is also utilized for data storage of the voltage signal from detector 18 to save the recorded signals for archiving and/or for post analysis of the signals and to calculate the voltage to a velocity for plotting and graphically displaying the plot. The computer 30 provides a visual readout of the skin displacement (blood pressure waveform) and/or the skin velocity (impedance waveform) on a monitor. The computer 30 can receive inputs from an electrocardiogram connected to the subject to receive the QRS complex, which is used to calculate systolic time interval parameters. The computer 30 has USB and BNC analog outputs and a graphical user interface. The computer 30 can be calibrated to correlate the velocity and motion of the skin surface 26 to the pressure of the blood in the artery beneath skin surface 26.

Figure 2A:
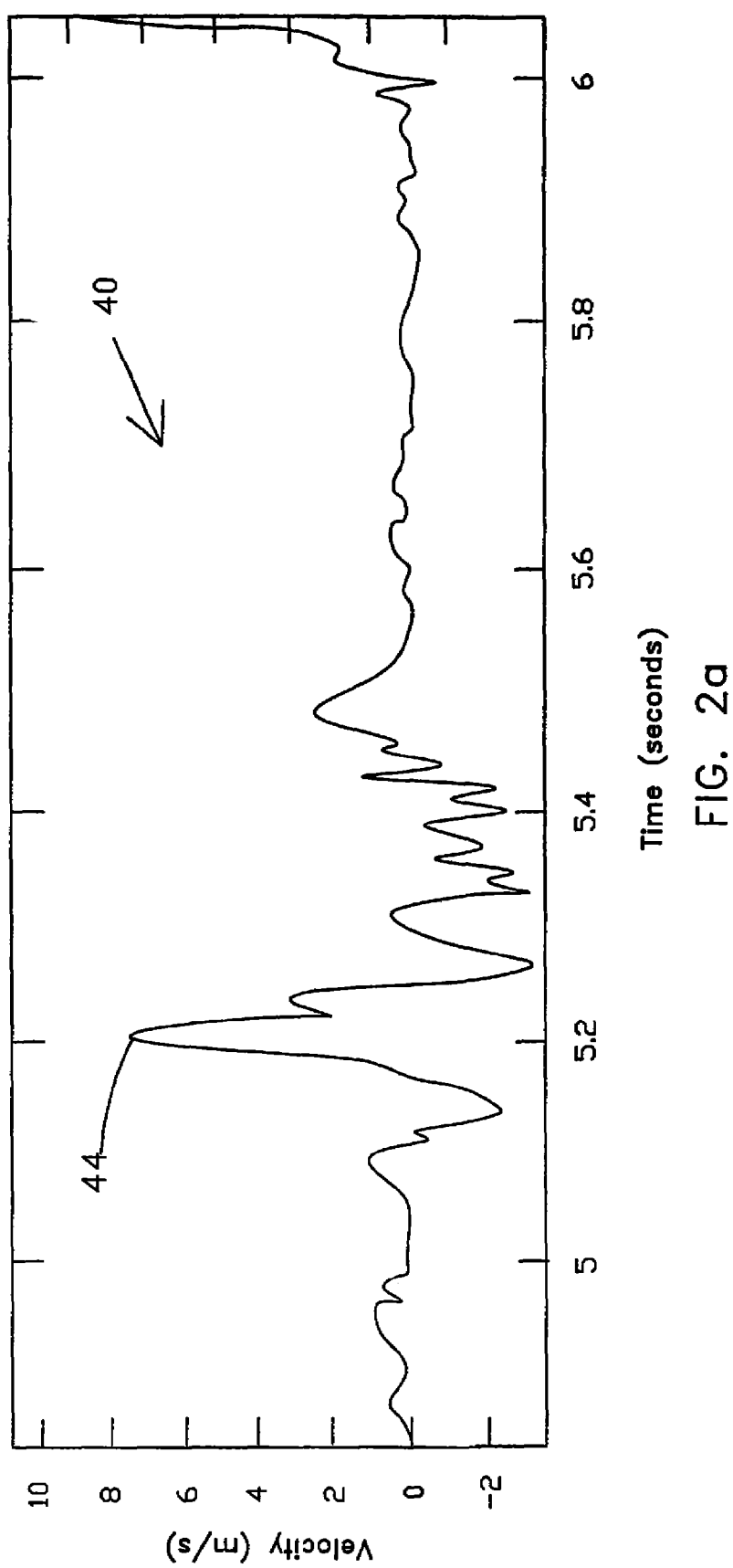
FIG. 2a is a graph of a blood pressure waveform obtained by measuring skin velocity in accord with the present invention for a single cardiac cycle.
Figure 2B:
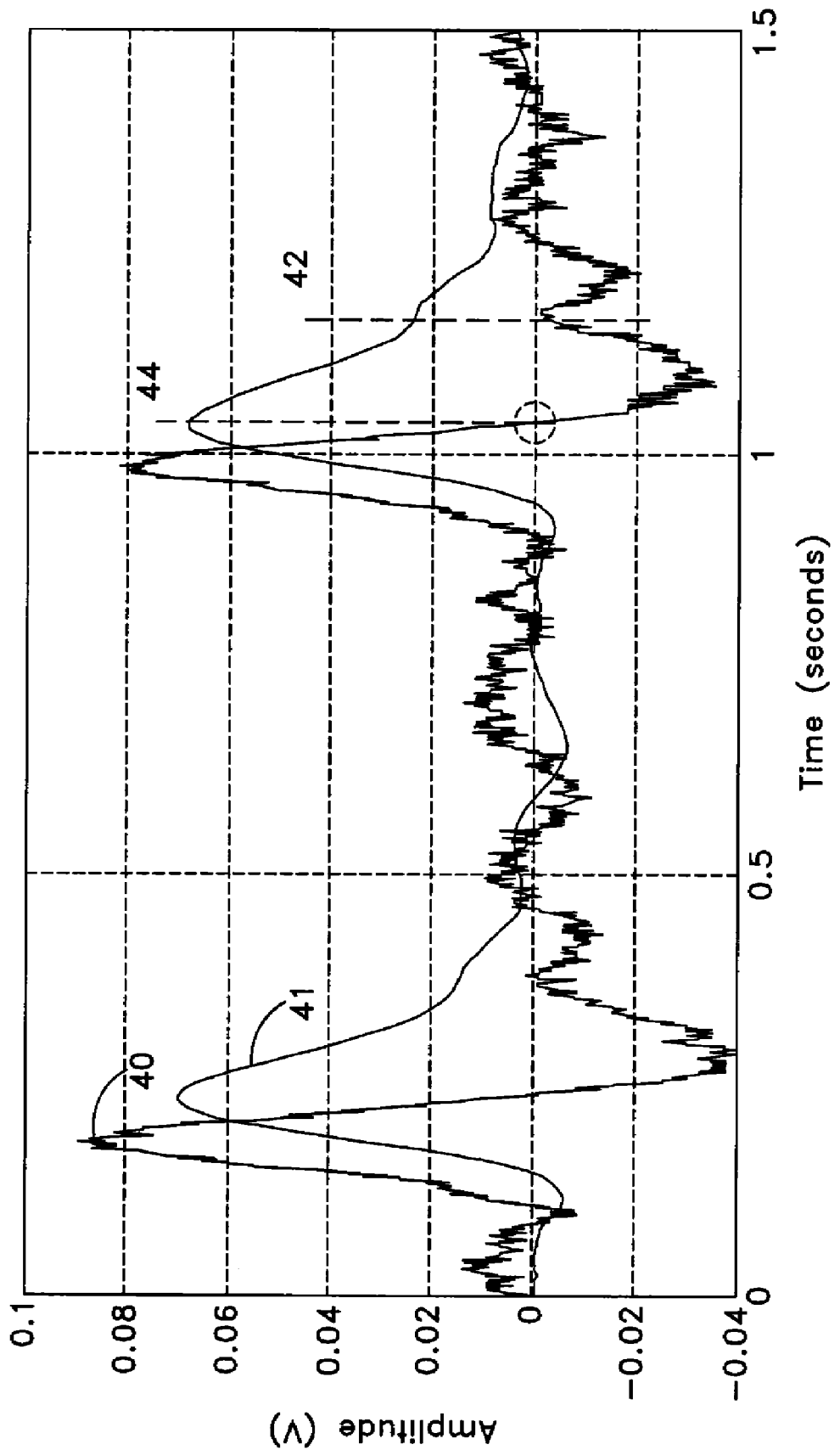
FIG. 2b is a graph of the LDV-measured velocity signal and the calculated displacement at the carotid artery for two cardiac cycles.
Figure 3A:
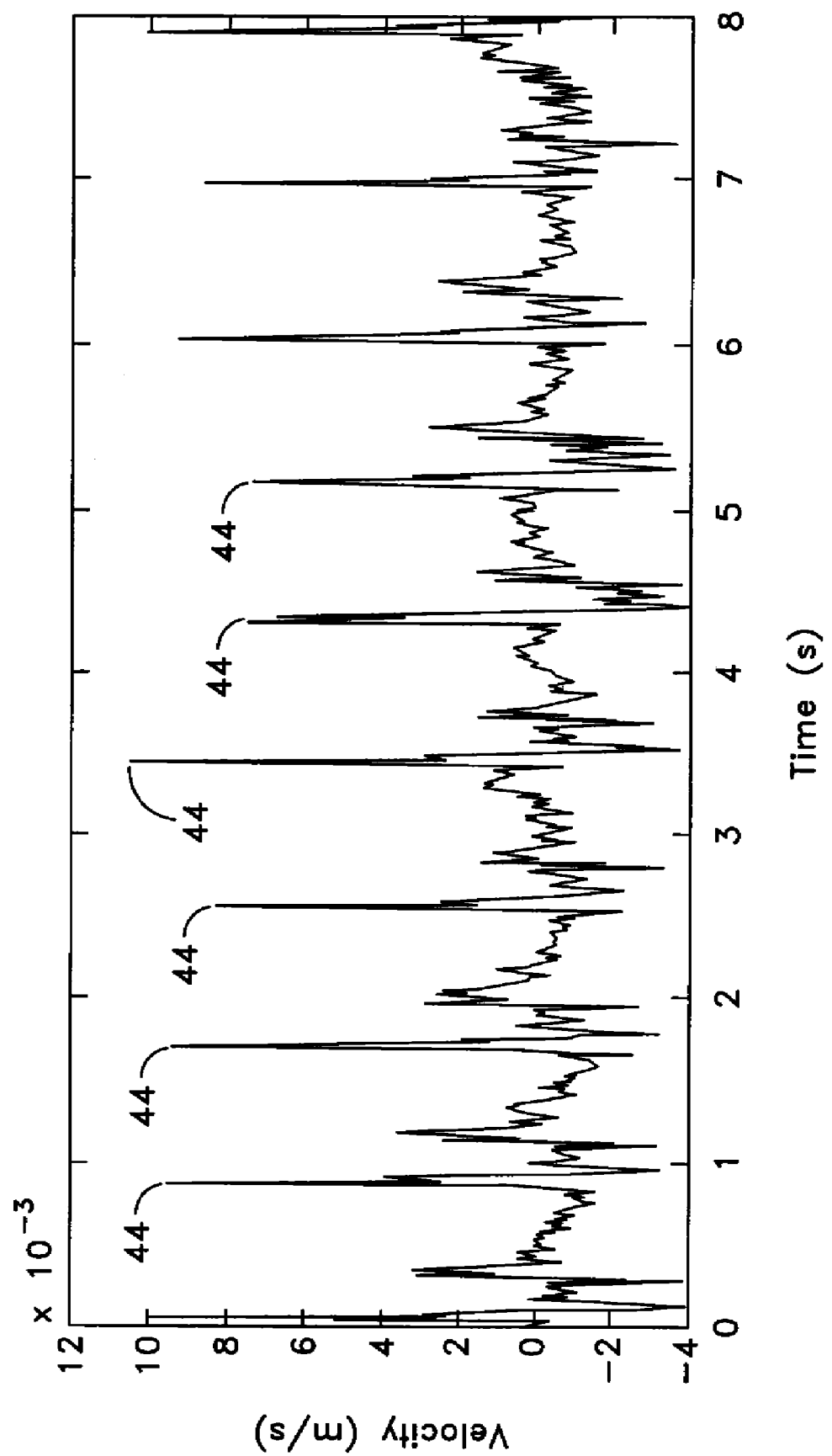
FIG. 3a is a graph of blood pressure waveform obtained by continuously measuring skin velocity for several cardiac cycles in accord with the present invention.
Figure 3B:
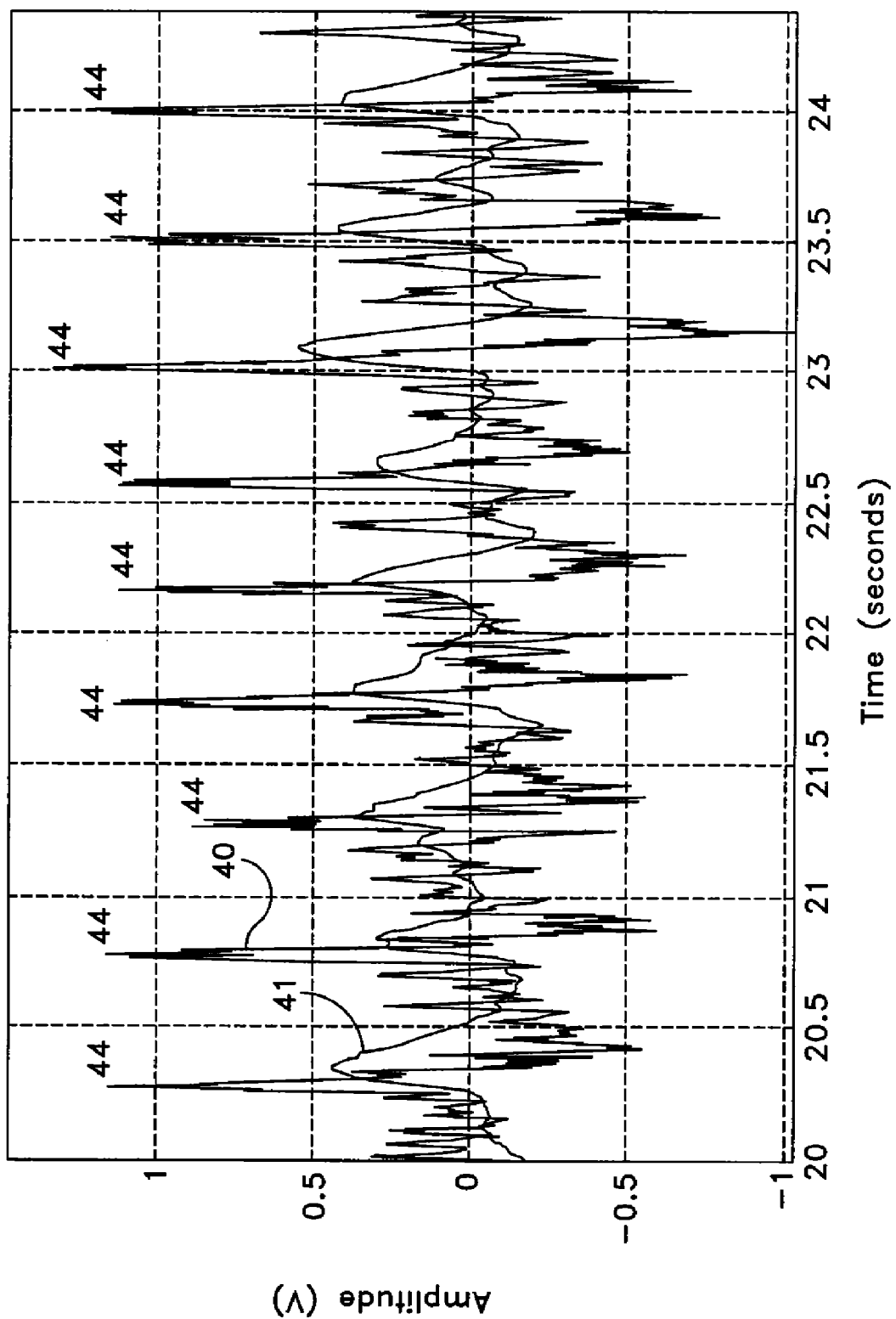
FIG. 3b is a graph of the simultaneous velocity and blood pressure (displacement) waveforms for a femoral artery signal. The displacement signal was calculated by integrating the measured velocity signal.

Utilizing the pulsation velocity of skin surface 26 over time, computer 30 can plot a highly accurate representative blood pulse waveform 40 represented as the skin velocity signal as indicated in FIG. 2a. The blood pressure waveform is obtained by integrating the velocity signal to obtain surface displacement 41 as indicated in FIG. 2b. Such a waveform is highly suitable for cardiac cyclic analysis. For instance, dicrotic notch 42, which indicates the closing of the aortic valve, is plainly visible in the displacement waveform 41 in FIG. 2b as is the peak systole 44. Heart rate is easily determined by calculating the time between the easily distinguishable peaks of successive velocity pulse waveforms 40 as indicated in FIG. 3a, or in the displacement waveform 41 in FIG. 3b, which shows multiple peak systoles 44 over a period of time. Once heart rate is determined, the PEP, LVET and QS2 can be derived from formulae (1), (2) and (3) as indicated above.

Thus, while the present invention does not directly measure arterial pressure, nonetheless it has been found by the inventors that the blood pressure waveform so obtained is quite suitable for timing analysis of the cardiac cycle to thereby evaluate cardiac function with timing events such as the systolic peak 44 and dicrotic notch 42.

It will be noted that all of the components of the laser Doppler vibrometer 12, including the laser source 14, the lens 16, and the detector 18, are preferably built into a single housing along with the glint tracking system 46 and are therefore more easily and quickly set up than prior art laser sensor instruments discussed herein. Moreover, suitable laser Doppler vibrometers are commercially available so that after review of the specification herein, one of skill in the art will be able to practice the invention.

The arterial pressure velocity waveform 40 obtained by laser Doppler vibrometer 12 or the calculated displacement waveform 41 may be analyzed to obtain various waveform characteristics. The timing of these waveforms may be combined with an electrocardiogram signal to estimate systolic time interval parameters. Alternatively, the systolic time interval may be estimated using heart rate information from the recorded waveform and applied to regression equations (1), (2), and (3).

While absolute blood pressures are not available directly from the present invention, such readings may be obtained by calibration techniques as described below. For example, a patient to be monitored during sleep may have the maximum/minimum blood pressures directly measured by existing contact means while awake to thereby calibrate the blood pressure waveform that is produced in accord with the present invention. Statistical techniques relating to expansion distances directly measured may be determined to estimate blood pressures in normal patients such as based on the amplitude of the movement parameters. Thus, the present invention might also be utilized to predict abnormalities due to deviations from anticipated values of absolute blood pressures determined statistically.

The advantages of the LDV/tracker/retro-reflector combination enhances the detection capabilities of the blood pressure waveform sensor providing a means of maintaining a continuous laser reflection back into the LDV from the retro-reflecting measurement surface to accommodate measurements where the subject has limited motion. It is necessary to convert the measured velocity into a skin displacement signal. This is a critical aspect of the invention in order to provide medical personnel a waveform that is similar to those achieved by catheter pressure sensor. However, further analysis of the velocity waveform may contain additional information beyond that observed in the displacement waveform.

The invention is practical to use on humans in places such as a trauma center and military medical facilities. This is because the optical sensor can be quickly administered to a patient to provide the medical staff with the waveform that provides information on the cardiac physiology of a patient. The information of the blood pressure waveform was a vital piece of information in additional to a patient's vital signs to indicate a patient's health status as used in a trauma center environment. The blood pressure waveform is not readily available without catheterization, which adds to patient distress. Likewise, field military application using the blood pressure waveform as an indicator of triage to determine which soldier's need immediate attention on the battlefield.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments, which would come within the spirit and scope of the present invention.

What is claimed is:

1. An apparatus for continuously measuring a physiological event of a subject, comprising:
    a first laser source capable of directing a laser beam toward the subject that will reflect said laser beam at a specific skin region of the subject wherein said skin region moves in response to said physiological event;
    a means for steering said laser beam emitted from the first laser source toward the subject such that as the subject physically changes location the laser beam is redirected to the specific skin region of the subject; and
    a detector comprising a laser interferometer that employs interferometer techniques to detect a reflected laser beam that is reflected off of the surface of the specific skin region that moves in response to said physiological event and determine at least a velocity of said moving skin region at the time the laser beam reflects off of the surface of the moving skin region.

2. The apparatus of claim 1, wherein said means for steering said laser beam emitted from the first laser source comprises:
    a laser tracker combined with said first laser source wherein said laser beam emitted from the first laser source is directed into said laser tracker; and
    a retro-reflective target that is disposed over said specific skin region wherein the retro-reflective target is capable of reflecting a laser beam off of the subject to the detector as well as back to the laser tracker.

3. The apparatus of claim 2, wherein said laser tracker comprises
    a second laser source capable of emitting a tracking laser beam;
    a beam combiner that combines said tracking laser beam with said laser beam emitted from the first laser source;
    a steering mirror that provides steering of the combined tracking laser beam and laser beam emitted from the first laser source;
    a tracking beam detector that detects the reflection of said combined tracking laser beam and laser beam emitted from the first laser source off of the retro-reflective target; and
    a programmable computer that is joined in communication with the tracking beam detector and steering mirror such that the programmable computer receives a signal from the tracking beam detector and controls the steering mirror-in response to the tracking beam detector's signal;
    wherein, both the laser beam emitted from the first laser source and tracking laser beam are directed onto the surface of the retro-reflective target and are steered by the steering mirror through a search pattern that is programmed into and implemented by the programmable computer until a reflection from the retro-reflective target is detected by the tracking beam detector.

4. The apparatus of claim 3, wherein said programmable computer is also joined in communication with said detector for analyzing said physiological event and converting the measured velocity of said skin region into a skin displacement signal.

5. The apparatus of claim 4, further comprising a single housing to contain said first laser source, said detector and said laser tracker.

6. The apparatus of claim 5, wherein said programmable computer produces a waveform representation of said physiological event by plotting said velocity and displacement of said skin region with respect to time and further comprising:
    a means for displaying said velocity and displacement with respect to time thereby displaying a measurement of said physiological event.

7. The apparatus of claim 6, wherein said physiological event is a blood pressure of the subject and wherein said waveform representation is representative of a blood pressure waveform and contains dicrotic notch information.

8. The apparatus of claim 7, wherein said programmable computer analyzes said blood pressure waveform to determine systolic time interval parameters.

9. The apparatus of claim 7, wherein said programmable computer analyzes said blood pressure waveform to determine heart rate.

10. The apparatus of claim 9, wherein said programmable computer compares systolic time interval parameters estimated utilizing said heart rate with systolic time interval parameters determined from said blood pressure waveform.

11. The apparatus of claim 6, wherein said physiological event is a rate of respiration of the subject.

* * * * *